United States Patent
Pernot

(10) Patent No.: US 10,131,756 B2
(45) Date of Patent: Nov. 20, 2018

(54) ARTICLE COMPRISING A POLYMERIC SUBSTRATE AND A LAYER OF SILICONE POLYMER

(71) Applicant: Laboratoires Urgo, Chenove (FR)

(72) Inventor: Jean-Marc Pernot, Dijon (FR)

(73) Assignee: LABORATOIRES URGO, Chenove (FR)

( * ) Notice: Subject to any disclaimer, the term of this patent is extended or adjusted under 35 U.S.C. 154(b) by 418 days.

(21) Appl. No.: 14/770,910

(22) PCT Filed: Feb. 27, 2014

(86) PCT No.: PCT/FR2014/050430
§ 371 (c)(1),
(2) Date: Aug. 27, 2015

(87) PCT Pub. No.: WO2014/131999
PCT Pub. Date: Sep. 4, 2014

(65) Prior Publication Data
US 2016/0009883 A1    Jan. 14, 2016

(30) Foreign Application Priority Data

Feb. 28, 2013 (FR) ..................... 13 51777

(51) Int. Cl.
| | | |
|---|---|---|
| A61L 15/26 | (2006.01) | |
| C08J 7/06 | (2006.01) | |
| B32B 27/28 | (2006.01) | |
| C08J 5/12 | (2006.01) | |
| A61L 15/18 | (2006.01) | |
| A61L 15/24 | (2006.01) | |
| A61L 15/40 | (2006.01) | |
| B32B 5/02 | (2006.01) | |
| B32B 27/12 | (2006.01) | |
| B32B 27/16 | (2006.01) | |
| A61F 13/02 | (2006.01) | |

(52) U.S. Cl.
CPC ............. *C08J 7/06* (2013.01); *A61F 13/0253* (2013.01); *A61L 15/18* (2013.01); *A61L 15/24* (2013.01); *A61L 15/26* (2013.01); *A61L 15/40* (2013.01); *B32B 5/022* (2013.01); *B32B 27/12* (2013.01); *B32B 27/16* (2013.01); *B32B 27/283* (2013.01); *C08J 5/12* (2013.01); *A61L 2420/02* (2013.01); *B32B 2255/205* (2013.01); *B32B 2262/0253* (2013.01); *B32B 2264/102* (2013.01); *B32B 2405/00* (2013.01); *B32B 2535/00* (2013.01); *C08J 2323/06* (2013.01); *C08J 2383/00* (2013.01)

(58) Field of Classification Search
CPC ......... B32B 27/08; B32B 25/08; B32B 25/20; B32B 27/28; B32B 27/12; B32B 5/022; C08J 5/12; C08J 7/06; A61L 15/16; A61L 15/40; A61L 15/26; A61L 15/24; A61L 15/18; A61F 13/0253
See application file for complete search history.

(56) References Cited

U.S. PATENT DOCUMENTS

| 6,475,329 | B1 | 11/2002 | Johnson et al. |
| 8,101,042 | B2 * | 1/2012 | Gantner .................. A61L 15/58 |
| | | | 156/249 |

FOREIGN PATENT DOCUMENTS

| EP | 2053161 | 4/2009 |
| EP | 2327544 | 6/2011 |
| WO | 2005/051442 | 6/2005 |
| WO | 2005/102403 | 11/2005 |
| WO | 2011137005 | 11/2011 |

OTHER PUBLICATIONS

Girschevitz et al., "Solution-Deposited Amorphous Titanium Dioxide on Silicone Rubber: A Confirmal, Crack-Free Antibacterial Coating," Chemistry of Materials, 20(4):1390-1396 (2008) XP055087664.
International Search Report in PCT/FR2014/050430 dated Jun. 5, 2014.

* cited by examiner

*Primary Examiner* — Ophelia A Hawthorne
(74) *Attorney, Agent, or Firm* — McAndrews, Held & Malloy, Ltd.

(57) ABSTRACT

Disclosed is an article that includes at least one polymeric substrate assembled on at least one layer of silicone polymer, characterized in that at least one of the polymeric substrate or the layer of silicone polymer has been brought into contact with particles of titanium dioxide, magnesium oxide and/or zinc oxide, before assembly of the article, and in that at least one of the polymeric substrate or the layer of silicone polymer has been brought into contact with water before or after assembly of the article. Also disclosed is a method of preparing the article, as well as the use of particles of titanium dioxide, magnesium oxide and/or zinc oxide, for improving the adherence between a polymeric substrate and a layer of silicone polymer.

26 Claims, No Drawings

ARTICLE COMPRISING A POLYMERIC SUBSTRATE AND A LAYER OF SILICONE POLYMER

CROSS-REFERENCE TO RELATED APPLICATIONS

The present application is filed pursuant to 35 U.S.C. 371 as a U.S. National Phase application of International Patent Application No. PCT/FR2014/050430, which was filed Feb. 24, 2014, claiming the benefit of priority to French Patent Application No. 1351777, which was filed on Feb. 28, 2013. The entire text of the aforementioned applications is incorporated herein by reference in their entirety.

BACKGROUND

The present invention relates to an article comprising a polymeric substrate on which a layer of silicone polymer is assembled, at least one of these two components having been brought into contact with particles of titanium dioxide, magnesium oxide and/or zinc oxide, and water, before or after assembly of said article.

Silicone derivatives are commonly used in a certain number of technical areas such as the cosmetic, aeronautical, automobile or medical areas, for example for coatings of plastics or textiles, for airbags, prostheses, implants, dressings, etc. The silicone gels or gums notably offer the advantage that they can be assembled onto a large number of supports while being inert for the organism, thus avoiding any problem of toxicity when they are used in human beings.

When silicone derivatives are used as coating elements of supports or as a layer affixed on said supports, it is often desirable to reinforce their adherence to the substrates on which they are deposited, so that the products thus treated can effectively withstand physical stresses, moisture or temperature variations.

It is known, for example, to treat the surfaces of supports or siliconized surfaces by corona treatment to modify the surface energy of said support, so as to improve adherence with the silicone derivative during deposition thereof. However, the levels of adherence obtained by corona treatment are not always sufficient, and, in the case of siliconized surfaces, this treatment may even impair the adhesive characteristics of the silicone.

Thus, new technologies have been developed to improve the adherence between a polymeric substrate and a layer of silicone polymer, notably with the use of bonding primers. Modification of the properties of adherence of siliconized surfaces by introducing bonding primers starting from the step of crosslinking of the silicone, directly within the reaction mixture containing the constituent precursors of the silicone, has notably been described in the literature. It has also been envisaged to deposit these bonding primers on a polymeric substrate, onto which the precursors of said silicone derivative will then be poured. In both cases, the end product offers levels of bonding that are slightly improved relative to a product that has undergone a corona treatment.

More recently, document WO 2005/051442 of the company Dow Corning Corporation proposed methods for improving the adherence of a silicone gel to the surface of a plastic polymeric substrate. This application teaches direct treatment of the substrate or silicone already synthesized by means of bonding primers of the titanate type, and preferably treatment of a silicone gel that has already been synthesized and crosslinked.

Thus, the use of bonding primers, notably primers of the titanate type, has been described for treating the substrate or the silicone derivative, either at the time of crosslinking, or once the substrate or the silicone derivative respectively has been synthesized or crosslinked.

However, more recently, application EP 2 053 161 of the company Dow Corning Toray partly adapted the teaching of application WO 2005/051442 with regard to the adhesion of a layer of silicone on a textile substrate. In this application, it was noted that bonding primers of the titanate type are unable to provide prolonged adhesion between a textile product and a layer of silicone, when these primers are incorporated in the reaction mixture constituting the future layer of silicone. The end product obtained by this method has inadequate levels of adherence, especially when it is submitted to large variations of temperature and humidity. This document recommends the use of bonding primers based on zirconium to ensure adhesion of a layer of silicone on a textile substrate.

Furthermore, the use of bonding primers of the titanate type poses problems both during use thereof and in the end product to which they are added. In fact, notably in order to avoid any contact with the water of the air, which could give rise to an anticipated chemical reaction, certain of these bonding primers, the most commonly used of which is titanium tetrabutanoate, are dispersed in an organic solvent. However, many problems of intolerance or even of toxicity are known, associated with the use of said solvents in the manufacture of an article such as that forming the subject matter of the present invention. It is also possible to use other types of bonding primers functioning in the aqueous phase, but whose results in terms of improvement of adherence are not satisfactory, and which moreover require the incorporation of additives (for example acetic acid) during use thereof and/or the application of a thermal treatment, said treatment being incompatible with the use of certain polymeric substrates.

Thus, the use of bonding primers of various types and notably of the titanate type causes many problems or complications associated with the application and use thereof. Moreover, the levels of adherence obtained by these treatments require further improvement.

SUMMARY

Therefore the applicant aimed to provide a novel product offering improved bonding between a layer of silicone polymer and a polymeric substrate, without using bonding primers of the titanate type, and offering the best possible guarantees with respect to health safety.

Thus, the present invention aims to propose novel articles based on a polymeric substrate and a layer of silicone polymer, in which the adherence of the silicone on the substrate is particularly high, said substrates being suitable moreover for medical or cosmetic applications without giving rise to problems of toxicity associated with the use of certain solvents.

More particularly, according to a first aspect, the invention relates to an article comprising at least one polymeric substrate assembled on at least one layer of silicone polymer, characterized in that at least one of the polymeric substrate or of the layer of silicone polymer has been brought into contact with particles of titanium dioxide, magnesium oxide and/or zinc oxide, before assembly of said article, and in that at least one of the polymeric substrate or of the layer of silicone polymer has been brought into contact with water before or after assembly of said article.

Particularly surprisingly, such an article displays levels of bonding between the polymeric substrate, which is preferably a textile, and the layer of silicone polymer, better than the known articles. These results are all the more unexpected since document EP 2 053 161 cited above strictly discouraged the use of compounds based on titanium for improving the adherence of textile products to a silicone derivative.

According to a second aspect, the invention also relates to a method of preparing an article as described above, comprising the following steps:

i. supplying or preparing a polymeric substrate,
ii. supplying or preparing a layer of silicone polymer,
iii. bringing at least one of the polymeric substrate or of the layer of silicone polymer into contact with particles of titanium dioxide, magnesium oxide and/or zinc oxide,
iv. bringing at least one of the polymeric substrate or of the layer of silicone polymer into contact with water before or after assembly of said article,
v. assembling the substrate and the layer of silicone polymer so as to form said article.

According to a third aspect, the invention also relates to the use of particles of titanium dioxide, magnesium oxide and/or zinc oxide, and preferably particles of titanium dioxide, for improving the adherence between a polymeric substrate and a layer of silicone polymer.

DETAILED DESCRIPTION

Article

The present invention relates to an article comprising at least one polymeric substrate assembled on at least one layer of silicone polymer, at least one of the polymeric substrate or of the layer of silicone polymer having been brought into contact with particles of titanium dioxide, magnesium oxide and/or zinc oxide, before assembly of said article, and at least one of the polymeric substrate or of the layer of silicone polymer having been brought into contact with water before or after assembly of said article.

Alternatively, the present invention relates to an article comprising at least one polymeric substrate assembled on at least one layer of silicone polymer, at least one of a precursor constituting the polymeric substrate or of a precursor of the layer of silicone polymer having been brought into contact with particles of titanium dioxide, magnesium oxide and/or zinc oxide, before assembly of said article.

"Precursor constituting the polymeric substrate" means any monomer or polymer capable of polymerizing or capable of being transformed to obtain the finished substrate. The precursor may thus be a monomer, a "prepolymer" or a polymer.

"Precursor constituting the layer of silicone polymer" means any compound capable of polymerizing to form the layer of silicone polymer.

The articles according to the present invention may find application in a large number of various technical areas such as building, aeronautical, automobile, the medical or cosmetic field, or textiles.

The article according to the invention may for example be a dressing, an orthosis, a prosthesis, a catheter, an implant, an article of clothing, an airbag etc.

According to a preferred embodiment, the article according to the invention is used in the medical field, and is preferably a dressing.

Polymeric Substrate

The article according to the present invention comprises at least one polymeric substrate.

Polymeric substrate means any macromolecular material, notably obtained by polymerization or transformation of at least one precursor (monomer, prepolymer or polymer). They may be synthetic or natural materials, for example textiles, composite materials, a combination of all of these materials or else a combination of different polymers within the same material and the combination of materials thus obtained.

According to a particular embodiment, the polymeric substrate employed in the context of the present invention is a polyolefin, and may notably be selected from the nonlimiting list of compounds comprising, among others, low-density or high-density polyethylenes, polypropylenes, polybutylenes, polymethylpentenes, and ethylene-vinyl acetate (EVA) polymers. The polymeric substrate may also be selected from the nonlimiting list of compounds comprising among others the vinyl polymers such as polyvinyl acetates, polyvinyl alcohol, polyvinylbutyral or polyvinylformal, the derivatives of polyvinyl chloride (polyvinyl chloride, polyvinylene chloride, polyvinylchloride-propylene copolymer); the polyurethanes and the urea-polyurethanes, the polystyrenes and copolymers thereof (styrene-butadiene copolymer, styrene-acrylonitrile copolymer, styrene-butadiene-acrylonitrile copolymer), and the derivatives of acrylic polymers (polyacrylates, polymethyl methacrylate, ethylene/butyl acrylate copolymer, ethylene/methyl acrylate copolymer, ethylene/methacrylic acid copolymer), polyacrylonitrile, the polyesters (notably PETE, polyethylene terephthalate, polybutylene terephthalate, polyvinyl acetate, the polylactic-glycolic derivatives), cellulose films (nitrocellulose, ethylcellulose, cellulose acetate, cellulose acetate butyrate, cellulose propionate), the polyimides, the polyamides (nylon), phenolic and epoxy plastics, polycarbonates, phenoplasts, fluorinated polymers (polytetrafluoroethylene, poly(vinylidene fluoride)), the polyoxymethylenes, polyphenylene oxides, polysulfones (PSU, PESU, PPSU), polyphenyl sulfide, and materials based on polysaccharides.

The polymeric substrate employed in the present invention may be in almost any of the possible forms. It may for example be a continuous or discontinuous plastic film, a woven, knitted or nonwoven material, a fibrous network or a foam.

According to a preferred embodiment, the polymeric substrate is in the form of a textile, preferably nonwoven, based on polyethylene. As examples of this type of substrate, we may notably mention the spunbonded nonwovens consisting of polyethylene fibers having a weight between 30 and 40 g/m$^2$, such as that marketed by the company Fiberweb under the name Berotex-PE® 35 g/m$^2$ or that marketed by the company Freudenberg under the name Vilmed® LSO 1040 WEISS.

In the context of the present invention, it is preferred to use a nonwoven, notably being in the form of a spunlaid voile having a weight between 5 and 80 g/m$^2$, and preferably between 20 and 50 g/m$^2$.

Silicone Polymer

The article according to the present invention also comprises at least one layer of silicone polymer.

The term polymer "layer" is used, in the context of the present application, when the silicone polymer is in the form of a continuous or discontinuous layer, of small thickness relative to the extent of its surface.

The silicone polymer should be selected so as to have optimal adherence on the patient's skin when the article is a dressing or a prosthesis. It should notably be soft and comfortable, flexible and strong, repositionable, and should not leave residues on the skin when it is removed.

The silicone polymer is preferably adhesive, physiologically acceptable for the skin, and its structure is at least partially crosslinked, preferably fully crosslinked.

Among the adhesive silicone polymers suitable for the present invention, a distinction is made between the adhesive silicone polymers that are gentle on the skin ("soft skin adhesives" (SSA)) and the pressure-sensitive adhesive silicone polymers ("pressure sensitive adhesives" (PSA)).

According to a preferred embodiment of the invention, the silicone polymer is an adhesive silicone polymer that is gentle on the skin (SSA). This polymer may be manufactured from silicone precursors that crosslink after being put in contact following a hydrosilylation reaction or a condensation reaction. Such systems are known from the prior art, for example in documents EP-A-0 251 810, EP-A-0 300 620 or U.S. Pat. No. 4,921,704. The mixtures of precursors described in these documents essentially comprise:
- a component A that comprises at least one polydimethylsiloxane substituted with a vinyl group at each end, and a platinum catalyst, and
- a component B of polydimethylsiloxane that comprises at least two hydrogenosilane groups.

Putting the two components in contact with one another causes a reaction of crosslinking of the two functionalized polydimethylsiloxanes, which takes place advantageously at room temperature and may be accelerated by heating.

The precursors of the adhesive silicone polymer may be selected from the following products: Silbione RT Gel® 4712 A&B and Silbione RT Gel® 4717 A&B from Bluestar Silicones, Wacker Silgel® 612 from Wacker-Chemie GmbH, Nusil; MED-6340, Nusil® MED-6345, Nusil® MEDS-6300, or Nusil® MED12-6300 from Nusil Technology, and D-7-9800® from Dow Corning.

According to another embodiment, the invention employs a pressure-sensitive adhesive (PSA) silicone polymer. This is preferably obtained from a silicone resin and liquid silicone. Such copolymers are described for example in "Silicone Pressure Sensitive Adhesive", Sobieski and Tangney, Handbook of Pressure Sensitive Adhesive Technology (D. Satas Ed.), Von Nostrand Reinhold, N.Y.

In this embodiment, the silicone resin is present at a level between 45 and 75% (relative to the total weight of silicone) and the liquid silicone is present at a level between 25 and 55%, with the sum of the percentages of silicone resin and of liquid silicone being equal to 100. Preferably, the silicone resin is present at a level between 55 and 65% (relative to the total weight of silicone) and the liquid silicone is present at a level between 35 and 45%, with the sum of the percentages of silicone resin and of liquid silicone being equal to 100.

Preferably, the silicone resin according to the invention is the product of condensation of $SiO_2$ groups and $R_3(SiO)_{1/2}$ (triorganosilyl) groups, for which each group R is selected independently from the methyl, ethyl, propyl or vinyl radicals and for which the ratio of the $SiO_2$ functions to the $R_3(SiO)_{1/2}$ functions of the silicone resin is from 0.6 to 0.9. Triorganosilyl groups usable for forming the silicone resin may be trimethylsilyl, triethylsilyl, methylmethylproprylsilyl, dimethylvinylsilyl units and mixtures thereof. The trimethylsilyl group is the one preferred in the context of the invention.

Preferably, the liquid silicone according to the invention is a diorganopolysiloxane with OH terminal functions having a viscosity between 100 and 100 000 cSt at 25° C. for which the substituents of the diorganopolysiloxane are selected independently from the methyl, ethyl, propyl or vinyl radicals. The diorganosiloxances are preferably linear polymers. Examples of diorganopolysiloxane may be, non-exhaustively, a polydimethylsiloxane, an ethylmethylpolysiloxane, a copolymer of dimethylsiloxane and methylvinylsiloxane, and mixtures of such polymers or copolymers having OH end groups. The diorganopolysiloxane preferred is a polydimethylsiloxane.

Examples of synthesis of such a copolymer are described for example in U.S. Pat. No. 5,162,410 or in patent CA711756.

The copolymers used according to the invention are marketed by Dow Corning under reference BIO-PSA®; these BIO-PSA® may be in two forms, standard or amine compatible, and are supplied in various solvents with several silicone resin/liquid silicone ratios. We may notably mention the grades 7-4400, 7-4500, 7-4600. The BIO-PSA® that is particularly preferred according to the invention is the 7-4400 grade.

The silicone polymer may comprise additives such as pigments, inhibitors or fillers, for example.

According to a particular embodiment, the layer of silicone polymer is discontinuous.

According to a more preferred embodiment of the invention, when the article is a dressing, the discontinuous layer of silicone polymer may constitute a coating of an openwork frame.

The frame may consist of any openwork material such as a perforated film, a thermoplastic filet, a textile for example a woven fabric, a knitted fabric, or a nonwoven, preferably elastic for better holding of the dressing on the skin. A perforated film will be for example of polyethylene or of polypropylene. A woven textile will be for example of polyethylene terephthalate or of polyamide. The weight of the frame is preferably between 10 and 500 g/m2, for example between 20 and 300 g/m2.

The frame may be coated with the silicone polymer on one of its faces, on both faces, or even on its entire surface. The size of the openings of the frame may be between 0.1 and 5 mm, for example between 0.5 and 3 mm. According to one embodiment, the silicone polymer constitutes the coating of a knitted fabric on its entire surface.

Particles of Titanium Dioxide, Magnesium Oxide and/or Zinc Oxide

In the context of the present invention, at least one of the polymeric substrate or of the layer of silicone polymer has been brought into contact with particles of titanium dioxide, magnesium oxide and/or zinc oxide, before assembly of the article according to this patent application, and at least one of the polymeric substrate or of the layer of silicone polymer has been brought into contact with water before or after assembly of said article.

Moreover, the applicant also envisaged that while bringing the precursors of the polymeric substrate or precursors of the layer of silicone polymer into contact with particles of titanium dioxide, magnesium oxide and/or zinc oxide, before or during synthesis of the layer of silicone polymer and/or synthesis of the polymeric substrate, it was also possible to increase significantly the adherence between the two elements once synthesized.

According to a preferred embodiment, the particles employed in the articles according to the invention are particles of titanium dioxide.

Bringing the polymeric substrate or layer of silicone polymer into contact with particles of titanium dioxide, magnesium oxide and/or zinc oxide, in the presence of water, differs from the treatments known from the prior art using bonding primers of these compounds, notably by the absence of a chemical reaction, such as, for example, a reaction of hydrolysis in the case of primers of the titanium tetrabutanoate type.

Now, the applicant observed, against all expectation, that treatments by means of particles of titanium dioxide, magnesium oxide and/or zinc oxide gave results for adherence far better than the treatments based on bonding primers, notably of the titanate type, known in the prior art.

According to one embodiment of the invention, the layer of silicone polymer can be brought into contact with particles of titanium dioxide, magnesium oxide and/or zinc oxide, preferably by dusting, and the polymeric substrate can be wetted, or humidified with an aqueous solution before assembly of the end product.

According to another variant of this particular embodiment of the invention, it is possible to wet the polymeric substrate once the latter is affixed on the layer of silicone polymer comprising, on its surface, particles of titanium dioxide, magnesium oxide and/or zinc oxide.

According to a particular embodiment, to facilitate wetting of the polymeric substrate when the latter is hydrophobic (notably polyethylene), it is possible, in the context of the present invention, to submit it additionally to a corona treatment before being brought into contact with water.

According to a particularly preferred embodiment, at least one of the polymeric substrate or of the layer of silicone polymer has been brought into contact with an aqueous dispersion of particles of titanium dioxide, magnesium oxide and/or zinc oxide.

According to a particular embodiment of the invention, the polymeric substrate and the layer of silicone polymer are both brought into contact with an aqueous dispersion of particles of titanium dioxide, magnesium oxide and/or zinc oxide.

Bringing the polymeric substrate or the layer of silicone polymer into contact with the aqueous dispersion of particles of titanium dioxide, magnesium oxide and/or zinc oxide may be carried out by any means known by a person skilled in the art, such as spraying, padding, or manual spreading, for example using a brush.

The particles of titanium dioxide, magnesium oxide and/or zinc oxide notably have a size ranging from 1 nm to 50 µm, preferably from 1 nm to 10 µm, and more preferably from 1 nm to 300 nm.

The particles of titanium dioxide, magnesium oxide and/or zinc oxide are notably present in the aqueous dispersion in a content ranging from 0.05 to 50 wt %, relative to the total weight of the dispersion, preferably from 0.1 to 20%, and more preferably from 0.5 to 5%. In any case, the particles of titanium dioxide, magnesium oxide and/or zinc oxide should preferably be present in a content sufficient to promote adhesion of the substrate or layer of silicone polymer on which they will be deposited, while being dispersed homogeneously in the aqueous phase.

The aqueous phase in which the particles of titanium dioxide, magnesium oxide and/or zinc oxide are dispersed comprises at least water.

The aqueous phase may, moreover, comprise any other physiologically acceptable, water-miscible organic solvent. According to the knowledge of a person skilled in the art, the water-miscible organic solvents that may be used in the aqueous dispersions of particles of titanium dioxide may make it possible to improve the affinity of the polymeric substrate for water, and may preferably be volatile, for example to accelerate drying of the polymeric substrate or of the silicone polymer after contacting.

Among the water-miscible organic solvents that may be used in the context of the invention, we may notably mention the monohydric lower alcohols having from 1 to 5 carbon atoms such as ethanol and isopropanol.

The water-miscible organic solvent, when it is present, should be added in a limited content so as not to pose any problem of toxicity or irritation. It may for example be added to the aqueous phase in a content ranging from 0.1% to 50 wt %, preferably from 0.5% to 10 wt %, relative to the total weight of the aqueous phase.

The aqueous dispersion may optionally comprise any additives, for example surfactants or hydrophilic gelling agents, for improving the dispersion of the particles of titanium dioxide, magnesium oxide and/or zinc oxide.

Method of Preparing the Article

The invention also relates to a method of preparing an article as described above, comprising the following steps:
i. supplying or preparing a polymeric substrate,
ii. supplying or preparing a layer of silicone polymer,
iii. bringing at least one of the polymeric substrate or of the layer of silicone polymer into contact with particles of titanium dioxide, magnesium oxide and/or zinc oxide,
iv. bringing at least one of the polymeric substrate or of the layer of silicone polymer into contact with water before or after assembly of said article,
v. assembling the substrate and the layer of silicone polymer so as to form said article.

According to one embodiment of the invention, in step iii, it is the layer of silicone polymer that is brought into contact with the particles of titanium dioxide, magnesium oxide and/or zinc oxide, preferably by dusting said particles on the layer of silicone polymer.

In this embodiment of the invention, step iv is carried out by wetting the polymeric substrate by means of an aqueous solution before assembly of the article.

Alternatively, step iv is carried out by wetting the polymeric substrate and the layer of silicone polymer by means of an aqueous solution after assembly of these components to form the article.

Thus, according to this alternative, the invention relates to a method of preparing an article as described above, comprising the following steps:
i. supplying or preparing a polymeric substrate,
ii. supplying or preparing a layer of silicone polymer,
iii. bringing at least one of the polymeric substrate or of the layer of silicone polymer into contact with particles of titanium dioxide, magnesium oxide and/or zinc oxide,
iv. assembling the substrate and the layer of silicone polymer so as to form said article,
v. bringing the polymeric substrate and the layer of silicone polymer into contact with water.

According to a particular embodiment, to facilitate wetting of the polymeric substrate when the latter is hydrophobic (notably polyethylene), it is possible, in the context of the present invention, to submit it additionally to a corona treatment before being brought into contact with water.

Thus the step of supplying or preparing a polymeric substrate comprises a subsequent step of corona treatment of said polymeric substrate before being brought into contact with water.

According to a preferred embodiment, the invention also relates to a method of preparing an article as described above, comprising the following steps:

i. preparing an aqueous dispersion of particles of titanium dioxide, magnesium oxide and/or zinc oxide,
ii. supplying or preparing a polymeric substrate,
iii. supplying or preparing a layer of silicone polymer,
iv. bringing the dispersion prepared in step i into contact with at least one of the polymeric substrate or of the layer of silicone polymer,
v. assembling the substrate and the layer of silicone polymer so as to form said article.

According to this embodiment, in step iv, it is the polymeric substrate that is preferably brought into contact with the aqueous dispersion of particles of titanium dioxide, magnesium oxide and/or zinc oxide. The step of bringing the aqueous dispersion of particles of titanium dioxide, magnesium oxide and/or zinc oxide into contact with the polymeric substrate is then followed by a step iv' of drying said impregnated polymeric substrate prior to assembly with the layer of silicone polymer.

Alternatively, in step iv, it is the layer of silicone polymer that may be brought into contact with the aqueous dispersion of particles of titanium dioxide, magnesium oxide and/or zinc oxide. The step of bringing the aqueous dispersion of particles of titanium dioxide, magnesium oxide and/or zinc oxide into contact with the layer of silicone polymer is then followed by a step v of assembly with the polymeric substrate, and then a step vi of drying of the article thus formed.

According to a preferred embodiment, it is the polymeric substrate that is brought into contact with the aqueous dispersion of particles of titanium dioxide, magnesium oxide and/or zinc oxide.

According to a very particular embodiment, the polymeric substrate may be prepared or supplied in a first step i, brought into contact with the aqueous dispersion of particles of titanium dioxide, magnesium oxide and/or zinc oxide, dried subsequently, and then the layer of silicone polymer is crosslinked in situ directly on said treated substrate. In this embodiment, the precursors constituting the layer of silicone polymer are thus deposited on the polymeric substrate, and then crosslinked directly on said substrate pretreated with the particles of titanium dioxide, magnesium oxide and/or zinc oxide.

The present invention is illustrated in more detail in the following nonlimiting embodiment examples.

Example

Three articles according to the invention were prepared by impregnation of a nonwoven based on polyethylene by means of a dispersion of particles of titanium dioxide in a first case, a dispersion of magnesium oxide in a second case and a dispersion of zinc oxide in a third case. A comparative article was also prepared by impregnation of a nonwoven based on polyethylene by means of bonding primers of the titanate type and a comparative article comprising a corona-treated nonwoven:

Article According to the Invention Comprising a Nonwoven Impregnated by Means of a Dispersion of Particles of Titanium Dioxide:

A 1 wt % dispersion of particles of titanium dioxide ($TiO_2$) in water was prepared as follows:

A beaker was charged with 198 g of distilled water, which was stirred mechanically so as to create a vortex.

Then 2 g of $TiO_2$ powder was added, with the trade reference "transparent titanium dioxide PW" marketed by the company Sensient, and it was kept stirred to prevent the formation of aggregates or agglomerates. The dispersion has a viscosity close to that of water.

Once the aqueous dispersion of particles of $TiO_2$ had been obtained, a nonwoven based on polyethylene marketed under the name Berotex-PE® 35 g/m$^2$ by the company Fiberweb was immersed therein, and it was left to soak for 10 min.

The impregnated nonwoven was then put between two nonstick papers. The product was then compressed by rolling a 10-kg pressing roller to and fro twice with the aim of simulating the expressing operation of the padding process and the product was put in a stove at 70° C. for 15 min.

Five (5) samples, 50 mm wide and 150 mm long, were cut out of the polymeric substrate.

Five (5) samples were cut out of an openwork frame coated with the layer of silicone polymer (adhesive face of the product referred to by the name Novesil 703702, marketed by the company Zodiac Aerospace), 50 mm wide and 150 mm long.

Each sample of silicone polymer was deposited on a sample of nonwoven and the product was compressed by rolling a 4-kg pressing roller to and fro twice to ensure adhesion of the assembly.

Article According to the Invention Comprising a Corona-Treated Nonwoven Impregnated by Means of a Dispersion of Particles of Magnesium Oxide:

A second article according to the invention was prepared according to the same protocol, using a 2 wt % dispersion of particles of magnesium oxide (MgO) in water instead of the dispersion of titanium dioxide. In parallel, a polyethylene nonwoven marketed under the name Berotex-PE® 35 g/m$^2$ by the company Fiberweb was treated by passing under a 0.64 kW two-electrode corona source at a speed of 10 m/min at a distance of less than 2 mm.

Once the aqueous dispersion of particles of MgO was obtained, the nonwoven based on polyethylene was immersed therein, and it was left to soak for 10 min.

Corona-Treated Article According to the Invention Comprising a Nonwoven Impregnated by Means of a Dispersion of Particles of Zinc Oxide:

A third article according to the invention was also prepared according to the same protocol, using a 5 wt % dispersion of particles of zinc oxide (ZnO) in water instead of the dispersion of titanium dioxide.

In parallel, a polyethylene nonwoven marketed under the name Berotex-PE® 35 g/m$^2$ by the company Fiberweb was treated by passing it under a 0.64 kW two-electrode corona source at a speed of 10 m/min at a distance of less than 2 mm.

Once the aqueous dispersion of particles of MgO was obtained, the nonwoven based on polyethylene was immersed therein, and it was left to soak for 10 min.

Comparative Article Comprising a Nonwoven Impregnated with Titanium Tetrabutanolate (TnBT):

A solution of titanium tetrabutanoate (TnBT) was prepared at 5 wt % in isopropanol:

A beaker was charged with 190 g of isopropanol, which was stirred mechanically.

Then 10 g of titanium tetrabutanoate of trade reference "Tyzor® TnBT" marketed by the company Dorf Ketal was added, stirring until it had dissolved completely.

Once the solution of titanium tetrabutanoate was obtained, a nonwoven based on polyethylene marketed under the name Berotex-PE® 35 g/m$^2$ by the company Fiberweb was immersed therein, and it was left to soak for 10 min.

The impregnated nonwoven was then put between two nonstick papers. The product was then compressed by rolling a 10-kg pressing roller to and fro twice to simulate the expressing operation of the padding process and the product was put in a stove at 70° C. for 15 min.

Five (5) samples, 50 mm wide and 150 mm long, were cut out of the polymeric substrate.

Five (5) samples were cut out of an openwork frame coated with the layer of silicone polymer (adhesive face of the product referred to by the name Novesil 703702, marketed by the company Zodiac Aerospace), 50 mm wide and 150 mm long.

Each sample of silicone polymer was deposited on a sample of nonwoven and the product was compressed by rolling a 4-kg pressing roller to and fro twice to ensure adhesion of the assembly.

Comparative Article Comprising a Corona-Treated Nonwoven:

A polymeric substrate of the polyethylene nonwoven type marketed under the name Berotex-PE® 35 g/m² by the company Fiberweb is treated by passing under a 0.64 kW two-electrode corona source at a speed of 10 m/min at a distance of less than 2 mm.

Five (5) samples, 50 mm wide and 150 mm long, were cut out of the polymeric substrate.

Five (5) samples were cut out of an openwork frame coated with the layer of silicone polymer (adhesive face of the product referred to by the name Novesil 703702 and marketed by the company Zodiac Aerospace), 50 mm wide and 150 mm long.

Each sample of silicone polymer was deposited on a sample of nonwoven and the product was compressed by rolling a 4-kg pressing roller to and fro twice to ensure adhesion of the assembly.

Adherence Test

The adherence of the articles according to the invention and of the two comparative articles prepared above was then tested, applying standard NF EN ISO 11339-May 2010, with a test specimen width of 50 mm and a testing speed fixed at 300 mm/min for the T peeling test.

The samples were left to "climatize" i.e. to acclimate to the conditions of temperature and hygrometry of the test, for 10 minutes in an acclimated room.

For each sample of article, the polymeric substrate was detached from the layer of silicone polymer on a few cm at one end.

The end of the layer of silicone polymer is clamped in the upper jaw of the testing dynamometer, and that of the polymeric substrate is clamped in the lower jaw.

A pulling speed of 300 mm/min is selected.

The average force required for separating the nonwoven from the layer of silicone polymer is then recorded for each sample.

For wet decomplexing, carried out on the article according to the invention comprising a nonwoven impregnated by means of a dispersion of particles of titanium dioxide, the samples are placed for 24 h in a stove at 37° C. in a solution of NaCl, CaCl$_2$.

After said 24 h, they are left to drain for 10 min before carrying out the measurements.

Then the average force required for separating the nonwoven from the layer of silicone polymer is recorded for each sample.

The results are presented in the following tables:

|  | Results Dry decomplexing (cN/5 cm) |
|---|---|
| Article according to the invention (particles of TiO$_2$) | 367.7 |
| Article according to the invention (particles of MgO) | 333 |
| Article according to the invention (particles of ZnO) | 369.4 |
| Comparative article (titanium tetrabutanoate) | 247.2 |
| Comparative article (corona) | 139 |

|  | Results Wet decomplexing (cN/5 cm) |
|---|---|
| Article according to the invention (particles of TiO$_2$) | 318.5 |
| Comparative article (titanium tetrabutanoate) | 184.9 |
| Comparative article (corona) | Not relevant |

It is clear that the articles according to the invention comprising a silicone gel deposited on a nonwoven, previously brought into contact with an aqueous dispersion of TiO$_2$, MgO or ZnO, display adherence between the nonwoven and the silicone gel far better than the comparative articles comprising a silicone gel deposited on a nonwoven treated either with a titanium tetrabutanoate bonding primer or corona-treated.

The article according to the invention comprising a silicone gel deposited on a nonwoven, previously brought into contact with an aqueous dispersion of TiO$_2$, in addition displays excellent results in the wet decomplexing test.

It should be noted that, taking into account the poor results of decomplexing obtained in the dry with the corona-treated substrates, the wet decomplexing test was not considered to be relevant.

The invention claimed is:

1. An article comprising at least one polymeric substrate assembled on at least one layer of silicone polymer, wherein at least one of the polymeric substrate or of the layer of silicone polymer has been brought into contact with particles of titanium dioxide, magnesium oxide and/or zinc oxide, before assembly of said article, and in that at least one of the polymeric substrate or of the layer of silicone polymer has been brought into contact with water before or after assembly of said article.

2. The article as claimed in claim 1, wherein at least one of the polymeric substrate or of the layer of silicone polymer has been brought into contact with particles of titanium dioxide, magnesium oxide and/or zinc oxide, and water, before assembly of said article.

3. The article as claimed in claim 2, wherein the particles of titanium dioxide, magnesium oxide and/or zinc oxide are present in the aqueous dispersion in a content ranging from 0.05 to 50 wt %, relative to the total weight of the dispersion.

4. The article as claimed in claim 3, wherein the particles are present in the aqueous dispersion in a content range of 0.1 to 20% relative to the total weight of the dispersion.

5. The article as claimed in claim 1, wherein the particles of titanium dioxide, magnesium oxide and/or zinc oxide have a size ranging from 1 nm to 50 μm.

6. The article as claimed in claim 3, wherein the particles are present in the aqueous dispersion in a content range of 0.5 to 5% relative to the total weight of the dispersion.

7. The article as claimed in claim 2, wherein the aqueous phase of the dispersion comprises water and optionally any other physiologically acceptable water-miscible organic solvent.

8. The article as claimed in claim 2, wherein the particles of titanium dioxide, magnesium oxide and/or zinc oxide are in an aqueous dispersion.

9. The article as claimed in claim 1, wherein the polymeric substrate is in the form of a textile.

10. The article as claimed in claim 9, wherein the textile is a nonwoven based on polyethylene.

11. The article as claimed in claim 1, wherein the layer of silicone polymer consists of a physiologically acceptable silicone adhesive, and is at least partially crosslinked.

12. The article as claimed in claim 11, wherein the silicone polymer is fully crosslinked.

13. The article as claimed in claim 1, wherein the layer of silicone polymer is discontinuous.

14. The article as claimed in claim 13, wherein the discontinuous layer of silicone polymer constitutes the coating of an openwork frame.

15. The article as claimed in claim 5, wherein the particles have a size range of 1 nm to 300 nm.

16. The article as claimed in claim 5, wherein the particles have a size range of 1 nm to 10 µm.

17. The article as claimed in claim 1, wherein the article is used in the medical field.

18. The article as claimed in claim 17, wherein the article is a dressing.

19. The article as claimed in claim 1, wherein the particles are particles of titanium dioxide.

20. The article as claimed in claim 1, wherein the silicone polymer is obtained from silicone precursors that crosslink after they are brought into contact, by a hydrosilylation reaction or a condensation reaction.

21. The article as claimed in claim 1, wherein the layer of silicone polymer comprises additives selected from the group consisting of pigments, inhibitors and fillers.

22. A method of preparing an article as claimed in claim 1, comprising the following steps:
   i. supplying or preparing a polymeric substrate,
   ii. supplying or preparing a layer of silicone polymer,
   iii. bringing at least one of the polymeric substrate or of the layer of silicone polymer into contact with particles of titanium dioxide, magnesium oxide and/or zinc oxide,
   iv. bringing at least one of the polymeric substrate or of the layer of silicone polymer into contact with water before or after assembly of said article,
   v. assembling the substrate and the layer of silicone polymer so as to form said article.

23. The method as claimed in claim 22, comprising the following steps:
   i. preparing an aqueous dispersion of particles of titanium dioxide, magnesium oxide and/or zinc oxide,
   ii. supplying or preparing a polymeric substrate,
   iii. supplying or preparing a layer of silicone polymer,
   iv. bringing the dispersion prepared in step i into contact with at least one of the polymeric substrate or of the layer of silicone polymer,
   v. assembling the substrate and the layer of silicone polymer so as to form said article.

24. The method as claimed in claim 22, wherein step iv is carried out by wetting the polymeric substrate and the layer of silicone polymer by means of an aqueous solution after assembly of these compounds to form the article.

25. The method as claimed in claim 22, wherein the polymeric substrate prepared or supplied in step ii undergoes a subsequent step of corona treatment before being brought into contact with water.

26. The method as claimed in claim 22, wherein the particles are particles of titanium dioxide.

* * * * *